(12) United States Patent
Ammar

(10) Patent No.: US 6,319,957 B1
(45) Date of Patent: *Nov. 20, 2001

(54) METHOD FOR TREATING SKIN

(76) Inventor: Khodor Ammar, Via Degli Orti, 5, 40100 Bologna (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,986

(22) Filed: Dec. 24, 1997

Related U.S. Application Data

(63) Continuation of application No. PCT/IT96/00129, filed on Jun. 27, 1996.

(30) Foreign Application Priority Data

Jun. 30, 1995 (IT) .............................. TO95A0551

(51) Int. Cl.⁷ .............................. A61K 31/07; A61K 7/00
(52) U.S. Cl. .................... 514/725; 424/401; 514/844; 514/859; 514/863
(58) Field of Search .................... 424/401; 514/725, 514/844, 859, 863

(56) References Cited

U.S. PATENT DOCUMENTS

| | | | |
|---|---|---|---|
| 4,216,224 | * 8/1980 | Yu et al. | 424/286 |
| 4,247,547 | 1/1981 | Marks | 424/240 |
| 4,677,120 | * 6/1987 | Parish et al. | 514/549 |
| 5,043,356 | * 8/1991 | Fulton, Jr. | 514/549 |
| 5,498,420 | * 3/1996 | Edgar et al. | 424/450 |
| 5,514,672 | * 5/1996 | Bazzano | 514/168 |
| 5,686,086 | * 11/1997 | Yanagida et al. | 424/401 |

FOREIGN PATENT DOCUMENTS

| | | |
|---|---|---|
| 0 472 225 A3 | 12/1986 | (FR) . |
| 906000 | 11/1960 | (GB) . |
| WO 89/00157 | 1/1989 | (WO) . |
| WO 89/06977 | 8/1989 | (WO) . |
| WO 93/10754 | 6/1993 | (WO) . |

OTHER PUBLICATIONS

Buehler et al. "Survey of Organic Syntheses", 1970, pp. 802–804.*

* cited by examiner

Primary Examiner—Jose' G. Dees
Assistant Examiner—Marina Lamm
(74) Attorney, Agent, or Firm—Schlesinger Arkwright & Garvey, LLP

(57) ABSTRACT

Compositions based on glyco-alcohol, hydro-alcohol or glyco-hydro-alcohol solutions of a glycol or glyceric ester of retinoic acid, preferably in association with the ethyl ester of retinoic acid and with hydroquinone, have been found to be particularly effective, as such or in cream form, in eliminating unsightly skin disorders such as acne, wrinkles, scars, stretch marks, dark spots, etc., and in treating mycotic skin diseases and psoriasis.

4 Claims, No Drawings

METHOD FOR TREATING SKIN

This application is a continuation of PCT/IT96/00129 field Jun. 27, 1996.

TECHNICAL FIELD

The present invention relates to cosmetic compositions which may be applied to any part of the skin of the human body, including the scalp and genital organs, for effectively reducing and/or gradually eliminating unsightly skin disorders such as stretch marks, acne, scars, dark spots and incipient baldness, and which are also highly effective in, treating mycosis and psoriasis. The present invention also relates to a cosmetic method of employing such compositions.

BACKGROUND ART

Many people suffer from unsightly skin disorders caused by diseases or deterioration of more or less extensive portions of the skin, e.g. acne, scars resulting from accidents, wrinkles, stretch marks, blackheads, dark spots, and which are often accompanied by excessive sebum secretion and, at times, by actual diseases often caused by mycotic infections such as psoriasis, pityriasis, onychomycosis, etc.

At present, people suffering from such problems must use a variety of either medicinal or cosmetic products (antimycotics, wrinkle removers, etc.), each limited to the treatment of a specific disorder. Acne, for example, is treated using medicaments based on retinoic acid (tretinoin, isotretinoin), but which are indicated exclusively for the treatment of acne. In more serious cases, again of acne for example, recourse must be made to surgery to remove the affected skin portions, owing to the failure of known medicinal remedies not only to arrest the disease but also to even partly repair the damage already produced to the skin.

DISCLOSURE OF INVENTION

It is an object of the present invention to provide a cosmetic and, at the same time, antimycotic composition capable of regenerating the affected skin regions and so gradually reducing and eventually attenuating and/or eliminating the above disorders.

It is a further object of the present invention to provide cosmetic compositions which, in addition to being cosmetic, are also highly effective in the treatment of psoriasis, even severe, recurrent cases involving extensive skin regions.

According to the present invention, there is provided a cosmetic, antimycotic composition for skin application, in particular for treating unsightly skin disorders such as acne, stretch marks, scars and dark spots;

characterized by comprising at least a glycol or glyceric ester of retinoic acid dissolved in a glyco-alcohol, hydro-alcohol or glyco-hydro-alcohol solution.

Preferably, the composition also comprises, in combination, the ethyl ester of retinoic acid and hydroquinone, both also dissolved in said glyco-alcohol, hydro-alcohol or glyco-hydro-alcohol solution.

More specifically, said glyco-alcohol solution comprises propylene glycol and, in lesser proportions, ethyl alcohol; and also contains propylene glycol ether.

In the case in point, one composition according to the invention comprises a glyco-alcohol solution of 0.10 to 0.25 N of ethyl ester of retinoic acid, and 0.15 to 0.30 N of glycopropylene ester of retinoic acid. Preferably, said glyco-alcohol solution presents a propylene glycol base, and also contains 0.001 to 0.002 N of ethyl-glycopropylene ether.

As stated in the introduction, retinoic acid as such is already known as a product for the treatment of acne, and is preferably obtained from its ethyl ester. Its direct "clinical" use, however, in the form of ethyl and, more especially, glycopropyl ester, and its association with hydroquinone in a glyco- and/or hydro-alcohol solution, are entirely new, and have surprisingly resulted in a product which is equally effective in the treatment of any other unsightly skin disorder, and which produces a marked peeling effect (desquamation of the surface layers of the skin) with a visible improvement in the tone, firmness and luminosity of the skin, a visible reduction of small wrinkles, and a marked reduction of deeper wrinkles, together with a reduction in excess sebum secretion.

In the case of acne, repeated use of the composition according to the invention provides for a marked improvement after only a few applications (five on average) and eventually total elimination. The composition according to the invention is also a highly effective antimycotic for curing diseases such as pityriasis, versicolor and onychomycosis after only two/four applications (one a week), and also provides for a marked improvement and for eventually curing psoriasis.

Clinical tests have shown no appreciable side effects, with the exception of individual hypersensitivity to one of the components, and headaches accompanied or not by itching of the treated parts in the case of product abuse.

The composition according to the invention may be marketed and used in the form of a solution applied using cotton cloth, cotton-wool, tissues or sponges soaked in the solution, or may comprise solid or semisolid excipients in which the glyco-alcohol solution is dispersed to form a cream, in which case, however, the peeling effect is reduced or entirely eliminated.

According to a preferred embodiment of the present invention, the composition therefore also comprises solid or semisolid excipients in which 2–10% by weight of said glyco-alcohol, hydro-alcohol or glyco-hydro-alcohol solution of said esters of retinoic acid is dispersed, so that the composition according to the invention is in the form of a cream.

The composition according to the invention may optionally comprise a cortisone, an anti-inflammatory substance, one or more liposoluble vitamins, and salicylic acid as such or in the form of glycol ester. More specifically, said anti-inflammatory substance is selected from the group comprising: niflumic acid, indomethacin and naproxene.

Alternatively, the composition according to the invention may comprise sodium heparin in gel form to enhance the anti-edema effect.

The composition according to the invention is prepared by producing an esterification reaction between retinoic acid and propylene glycol in a glyco-alcohol solution with a large excess of propylene glycol, so that substantially all the retinoic acid in the solution is esterified; and, after the esterification reaction, the solution is used as such, without removing the surplus reactants or the reaction products. The reaction is preferably conducted in the presence of 1.35% to 23.9% by weight of hydroquinone in the glyco-alcohol solution, and by catalyzing the reaction by heating the reaction mixture and/or by performing the reaction in the presence of an acid substance, e.g. salicylic acid, hydrochloric acid or thionyl chloride.

It is a further object of the present invention to provide cosmetic methods of treating unsightly skin disorders such as acne, scars, stretch marks and dark spots, and enabling results at various levels ranging from simply invigorating "healthy" skin to gradually attenuating (and eventually eliminating or practically eliminating) the disorder.

In general, a cosmetic method in accordance with the present invention is characterized in that:

glycol or glyceric ester of retinoic acid is prepared in a glyco-alcohol solution by esterifying the acid with the corresponding polyalcohol and operating with a large excess of polyalcohol in the presence of hydroquinone; and the resulting solution, containing the ester produced by the reaction, and possibly aged in atmospheric air at ambient temperature, is subsequently applied to the skin region for treatment to produce surface peeling of the region.

According to a first embodiment of the above cosmetic method, the glycopropylene ester of retinoic acid is prepared in a first solution comprising propylene glycol as the only solvent and containing 0 to 8.5% by weight, of the total weight of the solution, of hydroquinone, by dissolving, in said solution, 0.01 to 4% by weight, of the total weight of the solution, of retinoic acid; and said solution containing the prepared ester is subsequently applied to the skin region for treatment.

According to a second embodiment of the cosmetic method according to the invention, a mixture of glycopropylene and ethyl esters of retinoic acid is prepared in a second solution comprising equal proportions by volume of ethyl alcohol and propylene glycol as solvents and containing 1 to 13% by weight, of the total weight of the solution, of hydroquinone, by dissolving, in said solution, 0.01 to 0.13% by weight, of the total weight of the solution, of retinoic acid; and said solution containing the prepared mixture of esters is then applied to the skin region for treatment.

According to a third embodiment of the cosmetic method according to the invention, said solutions containing the reaction products and formed as in the previous embodiments are mixed together to a predetermined ratio; the resulting solution being stored stably in a refrigerator, and being applied in a predetermined quantity to the skin region by means of a sponge, cotton cloth, cotton-wool or any other appropriate means soaked in the solution.

The two solutions are preferably mixed to a ratio of 1:1 to 1:1.5 by volume.

The combined solution formed in the third embodiment of the cosmetic method according to the invention is applied once a day for a period of 6 to 10 days, said application cycle being repeatable after a suspension of 4 to 6 months, or is applied twice a week for 6 to 7 weeks. Alternatively, appropriate excipients may be added to the combined solution to form a cream containing 2 to 10% by weight of said solution; and the cream is applied as such, with no appreciable peeling effect, once a day for a period of 3 to 6 months. Optionally, the solution and the cream may be applied jointly in the amounts and in the manner prescribed.

According to a variation of the cosmetic method according to the invention, said esterification reaction may be performed in the absence of hydroquinone in said glyco-alcohol solution, or by subsequently eliminating the hydroquinone from said reaction solution; the resulting solution then being diluted up to 30 times in propylene glycol and used to treat particularly delicate skin regions such as lips or genital regions.

The present invention also relates to the use of the active principle of the above compositions, i.e. the glycopropylene ester of retinoic acid, in the preparation of pharmaceutical compositions for local destructive treatment of tumorous cells.

Finally, the same active principle may also be used in the preparation of pharmaceutical compositions administered orally for the treatment of nerve disorders. Experiments conducted by the Applicant have, in fact, shown positive results in several patients suffering from various disorders of the nervous system and to whom a composition in accordance with the invention was administered orally. Though an in-depth toxicological investigation has not yet been conducted, oral administration of such compositions would appear to pose no toxicity problems. Indeed, retinoic acid and hydroquinone are already administered orally, and propylene glycol is also nontoxic at the low concentrations of the compositions according to the invention.

BEST MODE FOR CARRYING OUT THE INVENTION

Further characteristics and advantages of the invention will be made clear in the following examples of a number of non-limiting embodiments.

EXAMPLE 1

A first solution, referred to as "solution A", is prepared with the following composition:

| | |
|---|---|
| retinoic acid | 0.89 g |
| hydroquinone | 50 g |
| ethyl alcohol | 400 ml |
| propylene glycol | 400 ml |

A second solution, referred to as "solution B", is also prepared with the following composition:

| | |
|---|---|
| retinoic acid | 1 g |
| hydroquinone | 28 g |
| propylene glycol | 530 ml |

In both of the above solutions, an esterification reaction between the alcohols and the acid is produced and accelerated, in the first case, by adding 1–3 drops of thionyl chloride to the solution as a catalyst, and, in the second case, by heating the solution to boiling point for 10–15 minutes. As opposed to thionyl chloride, the reaction may of course be catalyzed by other acid catalysts, such as hydrochloric or salicylic acid. The two solutions are then mixed together to a ratio of 1:1.325 to form a third solution, referred to as "solution S", which may be stored in a refrigerator and remains stable and active for 1–5 years.

EXAMPLE 2

Using solution S in Example 1, clinical tests were conducted of a test group of 30 patients affected with various types of unsightly skin disorders and/or diseases. More specifically, using a wad of cotton, a very small amount of solution S (2 ml for the face) is applied to the skin and, in the space of 2–3 days, produces a peeling effect (desquamation of the surface layers of the skin) lasting about 12–48 hours. This is at times preceded by reddening of the skin and a slight heating sensation, which ceases when the skin peels. The treatment may be repeated twice a week.

In a second test group of 30 patients with more serious disorders, the solution was applied daily for 6–20 days. A third test group of 30 patients were given a daily evening application of solution S in the form of a cream with 4% by weight of active substance (solution S), and 2% by weight for patients with sensitive skins. In no case was peeling produced. All three test groups treated as described above showed a visible improvement in skin tone, firmness and luminosity, accompanied by elimination of small wrinkles, a marked improvement in deeper wrinkles, and a gradual reduction of dark spots, excess sebum secretion and oiliness.

A fourth group of patients affected with acne and selected from the above three test groups underwent a combined treatment of a facial application of solution S twice a week for 6–7 weeks, followed by application of the 4% cream for 3 months. All patients showed a regression in the disease.

A fifth group of 30 patients with accident and/or surgical operation scars were treated with solution S once or twice a week and, at the same time, with a 5% cream for a period of 3 to 6 months. A marked improvement was seen in both old and new scars.

Solution S was also experimented on the above patients with a weekly application to the abdomen, breasts and buttocks for 6–10 weeks, and resulted in smooth skin and a marked attenuation of stretch marks.

Patients from the above five groups with scars on various parts of the body were treated with solution S two or three times a week, and every evening with a cream of 5–8% by weight of solution S. In 80–90% of the patients, second- and third-degree burn scars regressed in 3–6 months.

EXAMPLE 3

In the same way as in Example 1, a solution "M" was prepared with the following composition:

| | |
|---|---|
| retinoic acid | 2.5 g |
| hydroquinone | 109 g |
| propylene glycol | 1000 ml |

Patients selected from the five groups in Example 2 and suffering from mycotic infections were treated with solution M once or twice a week for 1–2 weeks. In all cases, a marked antimycotic action was observed, and patients suffering from pityriasis, versicolor or onychomycosis were cured completely.

Thirty patients, 12 of whom in serious conditions, with psoriasis on all parts of the body and treated for several years with various available therapies, were treated with solution M and solution S in Example 1, as follows:
- two applications a week of solution S and simultaneous application of cream with 6–10% of solution S for 1–4 months;
- in more stubborn cases, the cycle was repeated with solution M as opposed to S.

The disorder is cured first on the face, then on the back, chest and arms, and finally on the legs and buttocks.

The whole body was treated, even lesions which had already been cured, and the treatment was continued for 1–2 months after the cure, in that relapses are frequent, though the newly formed lesions are less noticeable than before.

In the case of psoriasis of the nails, only the solution was applied once a day for 3–4 months. Nail growth was accelerated, and the liquid was seen to selectively blacken the affected regions while leaving the healthy regions their natural color.

Patients suffering from psoriasis of the scalp were also treated 3 times a week with solution S diluted 6% by weight in propylene glycol, and washing the hair 15 minutes after the application.

In all cases, itching, smarting and discomfort were eliminated immediately.

Solution M was also used for locally treating external anal rhagades. 1 cc of the solution was applied locally once a day, two days a week, and brought about a complete cure in 2–4 weeks.

EXAMPLE 4

A test group of 1300 patients were treated with solutions S and M and a solution D identical to S but containing no hydroquinone, and using the solutions as such and in the form of cream.

The same results as in Examples 2 and 3 were observed, with absolutely no side effects. Patients in pregnancy or with skin tumors or allergies were not tested.

The solution in cream form provides for improving the skin but has no appreciable peeling effect.

The addition of small amounts of solution S (2 ml) provides for enhancing the anti-inflammatory effects of commercial medicinal products of niflumic acid 3% (cream), indomethacin 1% (gel) and naproxene 10% (gel); for enhancing the anti-edema effect of sodium heparin (gel); for producing an antipruritic effect with an aqueous extract of tritiam vulgaris (cream); for improving the anti-pityriasis effect of terbinafin 1% (cream); and for improved treatment of herpes simplex with aciclovir 5% (cream).

Solution M in a 2% cream and Diazepam 50 mg has a sedating-tranquillizing effect, which, however, still remains to be confirmed by parallel placebo testing.

Solution S diluted in a 1% water solution and applied to the scalp once a day for several months arrests falling hair, eliminates dandruff and itching, and, after about 1 month, stimulates the growth of hair in regions affected by baldness.

Solution S diluted up to 30 times in propylene glycol was also tested on delicate regions such as lips and genitals, or in the case of a particularly intense response, and confirmed the above results.

EXAMPLE 5

A number of compositions were prepared comprising: retinoic acid 2 g, salicylic acid 2–20 g, hydroquinone 10–50 g, and propylene glycol diluent 1000 ml. Some were esterified at ambient temperature, and others by heating to boiling point. When tested clinically, the resulting solutions, both as such and diluted in ethyl alcohol, appeared more active than those of similar composition in the previous Examples. Compositions identical to the above, but using a diluent of ethyl alcohol as opposed to propylene glycol, were also prepared. When esterified, the resulting solutions proved particularly effective in curing specific cases of eczema.

EXAMPLE 6

In a solution of 1 g of retinoic acid in 150 ml of propylene glycol, the acid was esterified by adding 1 mg of salicylic acid as a catalyst, and heating the solution to boiling point in a wide-bottomed vessel.

The resulting solution, referred to as "solution G", was administered orally to a test group of 55 patients suffering from various disorders of the nervous system, in particular cerebral ictus, senile cerebral atrophy, Alzheimer's disease, grave amnesia, suicidal depression, and serious peripheral neurological disorders. Children and patients in pregnancy were excluded.

A test group of patients suffering from the after-effects of cerebral ictus were administered orally with 1 cc of the solution every day for 15 days, and then 2–3 times a week. A marked improvement was observed in facial paralysis and ambulation, and a gradual improvement in the use of the affected leg. In patients suffering from acute cerebral ictus, daily administration of 4 cc of the solution seems to afford cerebral protection against necrosis.

Patients of over 90 years of age were administered 1 cc of solution every day for 10 days, then 2–3 times a week for 4 weeks, and finally once a week. Results showed an improvement in memory and cognitive capacity, and a reduction in anxiety and depression. An overall improvement in psychic condition was also observed in depressed, anxiety-prone and even suicidal patients subjected to the same treatment.

Improvements were also observed in the ambulation of patients affected with nerve disorders as a result of AIDS, and in the respiration of patients affected with chronic asthmatic bronchitis.

Epileptic patients administered with 1 cc a day of the solution showed a reduction in epileptic fits and an overall improvement in psychic condition.

A 12-year-old patient affected with Rett's syndrome, and suffering from paralysis of the legs for six months, regained use of the legs with a very small dose of the solution administered every other day.

Results showed a rapid improvement in patients suffering from pains caused by peripheral neural disorders, and a complete return to normal in patients suffering from sensitivity disorders.

Results also showed a rapid elimination of headaches, relief from pain in patients suffering from lumbar arthrosis, and an improvement in hyperthyroidism. The solution also seems to afford protection in cases of heart attack accompanied by arrhythmia, and to accelerate the healing of bone fractures (a thigh-bone fracture of a 5-year-old dog was healed after only 5 days' treatment). Finally, a patient suffering from pulmonary metastasis as a result of breast cancer, and already operated two years previously, was cured.

The solution has proved effective both at the initial and maintenance stages, even when diluted to a ratio of 1:16, and particularly if administered several times a day, up to a 0.001% by weight concentration of propylene glycol ester of retinoic acid.

The only side effects observed were headache and drowsiness in two patients subjected to high-dose treatment (15 cc), and the appearance of brown skin marks in a third patient.

Blood tests conducted after 2–3 months of daily treatment proved normal.

Solution G, alone or mixed to a ratio of 4:1 with solution M in Example 3, was also experimented in the local treatment of urogenital disturbances.

In one case of trigone cancer, irrigation of the bladder with 5 cc of solution G once a day for 10 days and subsequently twice a week produced an inflammatory leukolymphocytic reaction, with necrosis and breakdown of the tumor, and a cure after two months' treatment, as confirmed by cytoscopic and biopsy tests.

In a female patient with a trigone polyp, daily irrigation of the bladder with 5 cc of solution G mixed to a ratio of 4:1 with solution M in Example 3 brought about the destruction and elimination of the polyp after only one week's treatment.

Several other patients subjected to the same treatment showed improvements in the functioning of the neck of the bladder, bladder contraction, cystitis, prostate hypertrophy, urine discharge and post-urination residue. one case of regressed ejaculation as a result of radiation therapy was restored to normal in one week. Vaginal application of 1cc of solution G brought about a reduction in vaginitis and vaginal itching, and elderly patients showed an overall improvement in the vaginal mucous membrane.

Solution G has also proved effective when esterified in the absence of a catalyst, and by heating the solution to boiling point in a small-bottomed vessel for 4 hours.

EXAMPLE 7

The solutions prepared as described in the previous examples were subjected to standard chromatographic analysis, and all showed the presence of the propylene glycol ester of retinoic acid. In particular, the compositions administered orally showed a 0.015 N concentration of the ester (undiluted solutions), which may therefore reasonably be assumed to constitute the active principle (or at least one of the active principles) of the compositions according to the invention.

Said ester is believed to present highly effective anti-inflammatory properties, especially at low concentrations, and at the same time, especially if used at relatively high concentrations, to induce an aggressive tissue reaction such, for example, as to produce peeling of the skin and, as seen, the destruction of tumorous cells.

Chromatographic analysis also confirmed, when present, the effective catalytic action of salicylic acid (the salts and esters of this acid are only present in very low concentrations) and the stabilizing and antioxidizing effect of hydroquinone.

What is claimed is:

1. A method for preparing and using a therapeutic antimycotic composition capable of treating acne scars, stretch marks, scars and dark spots, the method comprising the steps of:

a) providing a retinoic acid with an excess amount of propylene glycol in a glyco-alcohol solution;

b) generating an esterification reaction sufficient to produce a composition, the reaction occurring between the retinoic acid and the propylene glycol so that substantially all of the retinoic acid is esterified and the esterification reaction is conducted in the presence of about 1.35% to about 23.9% by weight of a hydroquinone dissolved in the glyco-alcohol solution, the esterification reaction being accelerated by at least one of a catalyst or heating of the reaction mixture;

c) obtaining the composition following esterification without removal of surplus reactants or reactant products; and d) topically applying the obtained composition to the skin in an effective amount sufficient to cause a peeling and antimycotic effect to the skin and a reduction of one or more of acne scars, stretch marks, scars and dark spots on the skin.

2. The method of claim 1 and wherein:

a) the catalyst is salicylic acid.

3. The method of claim 1 and wherein:

a) the catalyst is thionyl chloride.

4. The method of claim 1 and wherein:

a) the catalyst is hydrochloric acid.

* * * * *